US010663760B2

(12) United States Patent
Heacock

(10) Patent No.: US 10,663,760 B2
(45) Date of Patent: May 26, 2020

(54) MOLDED OPHTHALMIC CONTACT LENS

(71) Applicant: Katena Products Inc., Denville, NJ (US)

(72) Inventor: Gregory Heacock, Maple Valley, WA (US)

(73) Assignee: Katena Products, Inc., Denville, NJ (US)

( * ) Notice: Subject to any disclaimer, the term of this patent is extended or adjusted under 35 U.S.C. 154(b) by 0 days.

(21) Appl. No.: 15/046,795

(22) Filed: Feb. 18, 2016

(65) Prior Publication Data
US 2016/0161762 A1 Jun. 9, 2016

Related U.S. Application Data

(63) Continuation-in-part of application No. 14/482,766, filed on Sep. 10, 2014, now Pat. No. 10,353,118.

(51) Int. Cl.
*G02C 7/02* (2006.01)
*G02C 7/04* (2006.01)
(Continued)

(52) U.S. Cl.
CPC .............. *G02C 7/04* (2013.01); *G02B 1/041* (2013.01); *G02B 3/00* (2013.01); *G02C 7/049* (2013.01)

(58) Field of Classification Search
CPC . G02C 7/02; G02C 7/061; G02C 7/06; G02C 2202/22; G02B 1/041
(Continued)

(56) References Cited

U.S. PATENT DOCUMENTS 3,589,800 A 6/1971 Cardona
4,728,183 A 3/1988 Heacock et al.
(Continued)

FOREIGN PATENT DOCUMENTS

| JP | H10174676 A | 6/1998 |
| JP | 2004318055 A | 11/2004 |
| WO | 2012064458 | 5/2012 |

OTHER PUBLICATIONS

International Search Report and Written Opinion From PCT Patent Application No. PCT/US2015/44975 dated Nov. 19, 2015 (8 pages).
(Continued)

*Primary Examiner* — Bumsuk Won
*Assistant Examiner* — Henry A Duong
(74) *Attorney, Agent, or Firm* — McAndrews, Held & Malloy, Ltd.

(57) ABSTRACT

Molded ophthalmic lenses with improved optical qualities can be manufactured at high volumes at low costs to provide single-use lenses. These ophthalmic lenses are contact lenses for examination or treatment of the interior of an eye, are formed of a moldable material, and have a ring portion integral with an optical and eye contacting portions. The ring portion extends from the main body and the ratio of the height of the ring portion to thickness of the lens is about 0.1 to 0.2. These features reduce production costs and improve the optical quality of the lens including allowing any debris, bubbles and the like that tend to adhere to the surface of the mold during the molding process to collect away from the optical centerline of the lens so as to improve the optical quality of the molded ophthalmic lens and minimizing shrinkage during the molding process.

18 Claims, 4 Drawing Sheets

(51) Int. Cl.
*G02B 3/00* (2006.01)
*G02B 1/04* (2006.01)

(58) Field of Classification Search
USPC .......................................... 351/159.1, 159.01
See application file for complete search history.

(56) References Cited

U.S. PATENT DOCUMENTS

| | | | |
|---|---|---|---|
| 5,046,836 A | 9/1991 | Volk | |
| 5,319,007 A * | 6/1994 | Bright .............. | B29D 11/00182 |
| | | | 351/159.01 |
| 5,333,017 A | 7/1994 | Volk | |
| 5,430,506 A | 7/1995 | Volk | |
| 5,523,810 A | 6/1996 | Volk | |
| 5,526,189 A | 6/1996 | Heacock | |
| 5,784,147 A * | 7/1998 | Volk ....................... | A61B 3/125 |
| | | | 351/205 |
| 6,019,472 A | 2/2000 | Koester et al. | |
| 6,120,147 A * | 9/2000 | Vijfvinkel .............. | A61B 3/125 |
| | | | 351/159.02 |
| 6,412,946 B1 * | 7/2002 | Vijfvinkel .............. | A61B 3/125 |
| | | | 351/159.02 |
| 8,303,116 B2 | 11/2012 | Heacock | |
| 2002/0159031 A1 | 10/2002 | Kanngiesser | |
| 2003/0095234 A1 * | 5/2003 | Heacock ................. | A61B 3/125 |
| | | | 351/219 |
| 2003/0147046 A1 | 8/2003 | Shadduck | |
| 2004/0080759 A1 | 4/2004 | Shaver | |
| 2005/0157260 A1 * | 7/2005 | Graham ................... | A61B 3/10 |
| | | | 351/219 |
| 2009/0244480 A1 * | 10/2009 | De Gaudemaris ....... | G02C 7/02 |
| | | | 351/159.41 |
| 2012/0113392 A1 * | 5/2012 | Heacock ................. | A61B 3/125 |
| | | | 351/219 |
| 2012/0242957 A1 | 9/2012 | Mordaunt | |
| 2015/0277088 A1 | 10/2015 | Chang | |
| 2015/0286068 A1 | 10/2015 | Chene et al. | |

OTHER PUBLICATIONS

PCT/US2015/044975 International Preliminary Report, dated Mar. 23, 2017.
International Search Report for PCT/US2017/018088 dated May 22, 2017.
Supplemental Partial European Search Result, EP15839624, dated May 11, 2018.
Extended Search Report, EP 15839624.2, dated Aug. 16, 2018.
International Preliminary Report, PCT/US2017/018068, dated Aug. 30, 2018.
Office Action issued by JP 2017-513054 dated May 25, 2017.

* cited by examiner

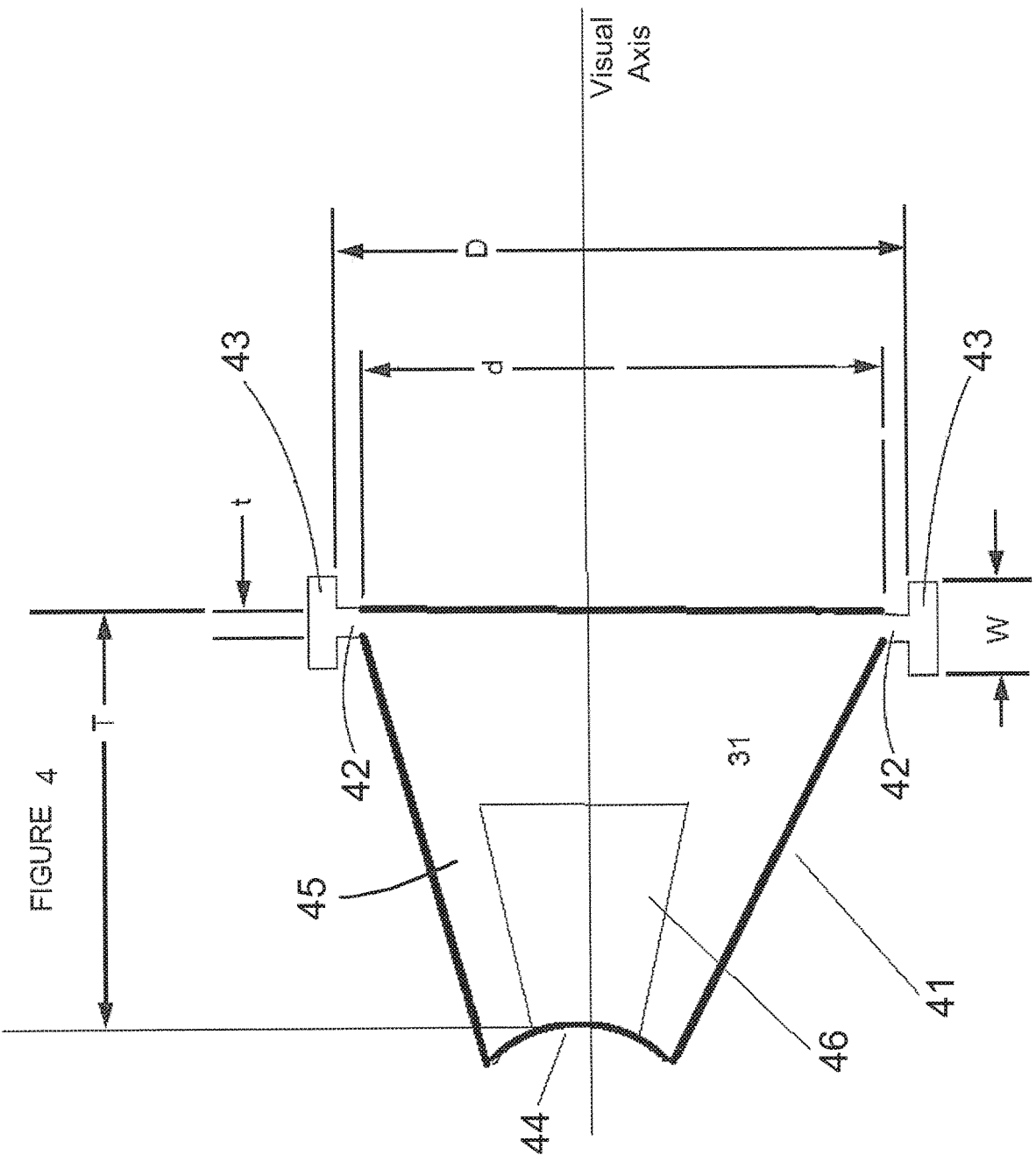

MOLDED OPHTHALMIC CONTACT LENS

RELATED APPLICATIONS

This application claims priority to and is a continuation-in-part of U.S. patent application Ser. No. 14/482,766 having a filing date of Sep. 10, 2014, which is incorporated herein by reference in its entirety.

TECHNICAL FIELD

This invention relates to molded ophthalmic lenses with improved optical qualities that can be manufactured at high volumes at low costs. For example, the invention relates to molded ophthalmic condensing lenses which provide a means for examination of the interior fundus of an eye. The invention relates to molded ophthalmic lenses which can be injection molded and/or, compression molded to provide a single use lens. The ophthalmic lens may have an integral ring and aspheric shape differing from known lenses of the same type to reduce cost and improve the optical quality of the lens. As another example, the invention relates contact lenses used by the clinician to view or treat the eye having a main body portion, a grip portion and an eye contacting portion. The invention relates to molded ophthalmic contact lenses which can be injection molded and/or, compression molded to provide a single use lens. The ophthalmic lens has an integral ring and shape differing from known contact lenses of the same type to reduce cost and improve the optical quality of the lens.

BACKGROUND

Ophthalmic lenses are used by ophthalmologists and optometrists for diagnosis and treatment of the eye. A common procedure performed by ophthalmologists is the examination of the interior of a patient's eye. This is an important procedure since variations in the appearance of the interior of a patient's eye can give an ophthalmologist important information on the health of a patient or the proliferation of a number of ocular diseases.

Commonly in an examination procedure, the ophthalmologist applies a topical drug to the patient's eye to dilate the pupil of the eye. Using a known condensing lens which the ophthalmologist holds in close proximity to the patient's eye in conjunction with an illumination system, the ophthalmologist is able to observe the interior of the patient's eye. These condensing lenses in general produce images that are useful to the ophthalmologist conducting the examination. The patient, however, must endure the various side effects of the dilation drug such as blurry vision, light hypersensitivity and poor depth perception. These side effects may persist up to several hours following an examination. Moreover, some patient's eyes do not dilate well, for example elderly patients or those taking certain medications.

U.S. Pat. No. 5,526,189, which is incorporated herein by reference, deals with a nonsymmetrical fundus observation lens or condensing lens with two aspheric surfaces which provides a means for examination of the interior of an eye and more particularly to a lens for observing a wide field of view image of the fundus of an eye through an undilated pupil.

Known ophthalmic lenses, including fundus observation lenses or condensing lenses, are generally machined and polished. Because such ophthalmic lenses are machined and polished, they are extremely costly to manufacture and cannot be produced in high volumes.

Instrument contamination and cross infection between patients is an ever present concern in the ophthalmic industry. Ophthalmic devices that must be sterilized between uses. However, this relies on personnel awareness, willingness to follow protocol, monitoring and documentation on the part of the ophthalmologist and his/her staff. Single-use devices can present a solution to this problem.

U.S. Pat. No. 8,303,116, which is incorporated herein by reference, deals with single-use, molded ophthalmic lenses that have improved optical qualities and that can be manufactured in high volumes at low costs. The lenses discussed therein have a portion that come into contact with the patient's eye and are differently-shaped than fundus observation lenses or condensing lenses.

As such, a single-use lens for use in indirect procedures, e.g. a fundus observation or condensing lens, is desirable and has not previously existed in the technical area. Similarly, a single-use lens for use in contact procedures is desirable and such a lens having the claimed shape has not previously existed in the technical area. Additional improvements are described herein.

BRIEF SUMMARY

The disadvantages of prior ophthalmic lenses have been overcome. In one embodiment, the present ophthalmic lenses have an optical portion with a proximal surface and an opposing surface and a ring portion extending circumferentially around the optical portion. The shape of the present lenses allows them to be used by ophthalmologists to view the interior of the patient's eye, e.g. the fundus, with or without dilation of the patient's eye. The shape of the present lenses also allows them to be formed by molding such as injection or compression molding. Since the lenses can be molded, they can be mass produced in large volume, i.e. they can be disposable or single-use.

In one embodiment, the present ophthalmic lens comprises an optical portion comprising a proximal surface and an opposing surface; and a ring portion extending circumferentially around the optical portion wherein the optical portion is formed of an optically transparent material. The lens is injection molded or compression molded which allows it to be single-use or disposable.

The ring portion can be integral with the optical portion and made of the same material as the optical portion. The axis of rotation of the ring portion can be perpendicular with the centerline of the lens.

The lens can further comprise a grip portion integral with the ring portion. As one example, the grip portion can be textured. Alternatively, the ring portion can act as a grip portion. In this alternative, the ring portion can be textured.

The lens can be formed of a material having a specific gravity of 1.1-1.2, such as 1.15-1.2. The material can have an index of refraction of 1.4 to 1.55. An example of such a material is polymethylmethacrylate.

The lens can have a thickness that is at least 10 mm, such as 10 to 20 millimeters. The lens can have a thickness ratio t/T of 0.015 to 0.2. The lens can have a diameter of at least 20 mm. The lens can have a diameter ratio d/D of 0.75 to 0.9. The lens can have a ratio of vertex curvature comparing the proximal surface to the opposing surface ranges between 1.5 and 2.0 times. The lens can have a focal length to thickness ratio F/T of 0.6-1.0. The lens can form a real image at a distance from the opposing surface of the lens that is between 5 and 40 mm.

The optical surfaces of the lens can be defined by the following formula:

$$z=Cr^2/(1+\sqrt{(1-(1+k)C^2r^2)})$$

A k value defining the surface lens can be within the range of −0.5 to −2.0.

The vertex radius (1/C) of a given surface can be within the range of 6.0 mm to 30 mm.

In another embodiment, the present ophthalmic lens comprises a main body portion comprising an optical portion and a ring portion extending circumferentially around the optical portion; and a grip portion wherein the optical portion comprises a proximal surface and an opposing surface and is formed of an optically transparent material. The lens is injection molded or compression molded which allows it to be single-use or disposable.

The ring portion can be integral with the optical portion and made of the same material as the optical portion. The axis of rotation of the ring portion can be perpendicular with the centerline of the lens. The grip portion can be textured.

The lens can be formed of a material having a specific gravity of 1.1-1.2, such as 1.15-1.2. The material can have an index of refraction of 1.4 to 1.55. An example of such a material is polymethylmethacrylate.

The lens can have a thickness that is at least 10 mm, such as 10 to 20 millimeters. The lens can have a thickness ratio t/T of 0.015 to 0.2. The lens can have a diameter of at least 20 mm. The lens can have a diameter ratio d/D of 0.75 to 0.9. The lens can have a ratio of vertex curvature comparing the proximal surface to the opposing surface ranges between 1.5 and 2.0 times. The lens can have a focal length to thickness ratio F/T of 0.6-1.0. The lens can form a real image at a distance from the opposing surface of the lens that is between 5 and 40 mm.

The optical surfaces of the lens can be defined by the following formula:

$$z=Cr2/(1+\sqrt{(1-(1+k)C2r2)})$$

A k value defining the surface lens can be within the range of −0.5 to −2.0.

The vertex radius (1/C) of a given surface can be within the range of 6.0 mm to 30 mm.

In yet another embodiment, the present molded ophthalmic lens comprises an optical portion comprising a proximal surface and an opposing surface having a ratio of vertex curvature comparing the proximal surface to the opposing surface ranging between 1.5 and 2.0 times wherein the lens is a single-use lens. The lens is injection molded or compression molded which allows it to be single-use or disposable.

The lens can further comprise a ring portion. The ring portion can be integral with the optical portion and made of the same material as the optical portion. The axis of rotation of the ring portion can be perpendicular with the centerline of the lens.

The lens can further comprise a grip portion integral with the ring portion. As one example, the grip portion can be textured. Alternatively, the ring portion can act as a grip portion. In this alternative, the ring portion can be textured.

The lens can be formed of a material having a specific gravity of 1.1-1.2, such as 1.15-1.2. The material can have an index of refraction of 1.4 to 1.55. An example of such a material is polymethylmethacrylate.

The lens can have a thickness that is at least 10 mm, such as 10 to 20 millimeters. The lens can have a thickness ratio t/T of 0.015 to 0.2. The lens can have a diameter of at least 20 mm. The lens can have a diameter ratio of 0.75 to 0.9. The lens can have a focal length to thickness ratio F/T of 0.6-1.0. The lens can form a real image at a distance from the opposing surface of the lens that is between 5 and 40 mm.

The optical surfaces of the lens can be defined by the following formula:

$$z=Cr^2/(1+\sqrt{(1-(1+k)C^2r^2)})$$

A k value defining the surface lens can be within the range of −0.5 to −2.0.

The vertex radius (1/C) of a given surface can be within the range of 6.0 mm to 30 mm.

In another embodiment, a contact lens can be formed using the same injection and/or compression molding; where a contact surface is suitably formed to contact the eye of the patient and where a main body portion incorporates a integral grip portion to facilitate manipulation by a doctor and further where the main body portion includes at least 1 mirror surface that allows the doctor to observe eye tissues located away from the normal visual axis of the lens. Thus in using the single piece contact lens, the doctor may observe tissue centrally located within the patient's eye by looking coincidentally with the visual axis of the lens, and the doctor may additionally be able to observe tissue within the eye of the patient that is located non axially by using a mirrored portion of the lens.

In one embodiment, the present ophthalmic lens comprises a ring portion, an eye contacting portion and a main body portion disposed between the ring portion and the eye contacting portion wherein the eye contacting portion, the main body portion and the ring portion are integrally formed and the lens has a height of the ring to thickness of the lens ratio of about 0.1 to about 0.2.

In certain embodiments, the lens can be formed of a material having a specific gravity of about 1.1 to about 1.9 and an index of refraction of about 1.4 to about 1.55. For example, the lens can be formed of a material having a specific gravity of about 1.1 to about 1.3. For example, the index of refraction can be between about 1.4 and about 1.55. For example, the lens can be formed of polymethylmethacrylate.

In certain embodiment, the lens can be injection molded or compression molded. The lens can be disposable.

In certain embodiments the lens can have the following dimensions. The lens can have a diameter ratio of about 0.75 to about 0.9. The lens can have a thickness of the lens that is at least about 10 mm. For example, the lens can have a thickness of the lens ranges from about 10 to about 20 mm. The lens can have a height of the ring portion is about 1 mm to about 7 mm.

In an embodiment, the lens can have an axis of rotation of the ring portion can be perpendicular with the centerline of the lens.

The lens can further comprise a grip portion integrally connected to the ring portion. The grip portion can be textured. In certain embodiments, the lens can have the following dimensions. The height of the grip portion can be about 3 mm to about 10 mm. The height of the grip portion to thickness of the lens ratio can be about 0.15 to about 0.3. The height of the grip to height of the ring ratio can be about 0.1 to about 1.0.

In one embodiment, the lens further includes an aluminum coating on a mirror surface. For example, the lens can have a single mirror with a width that is at least about 13.7 mm.

These and other objects, advantages and novel features of the present invention, as well as details of an illustrative embodiment thereof, will be more fully understood from the following description and the drawing.

BRIEF DESCRIPTION OF SEVERAL VIEWS OF THE DRAWINGS

FIG. 4 is a cross-sectional schematic view of a contact lens of one embodiment of the present invention shown.

Figure 1:
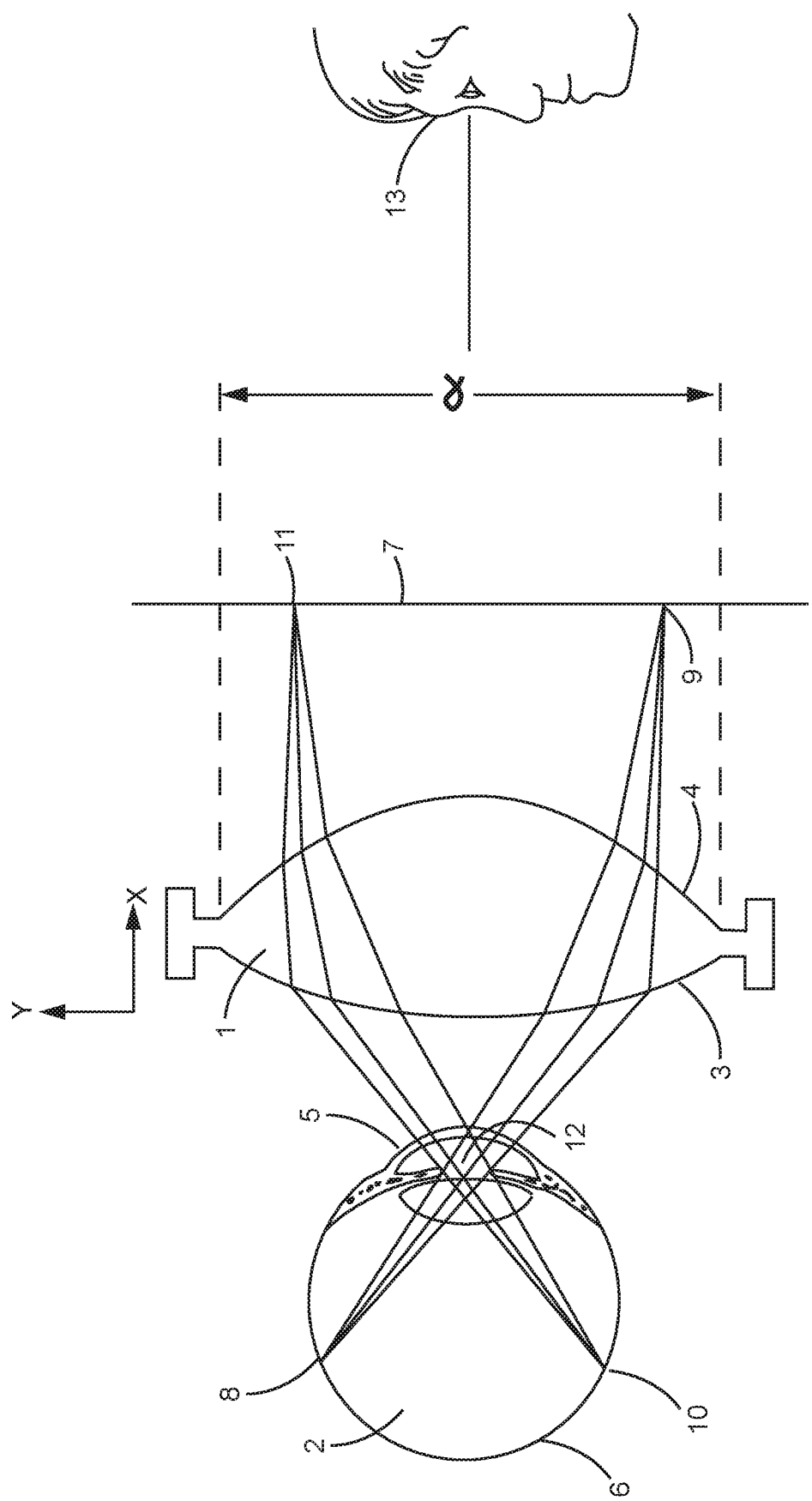
FIG. 1 is a cross-sectional schematic view of a fundus observation lens of one embodiment of the present invention shown in close proximity to a patient's eye.

The foregoing summary, as well as the following detailed description of certain embodiments of the present invention, will be better understood when read in conjunction with the appended drawings. For the purposes of illustration, certain embodiments are shown in the drawings. It should be understood, however, that the claims are not limited to the arrangements and instrumentality shown in the attached drawings. Furthermore, the appearance shown in the drawings is one of many ornamental appearances that can be employed to achieve the stated functions of the system.

DETAILED DESCRIPTION

This invention relates to a molded ophthalmic lens with improved optical qualities that can be manufactured at high volumes at low costs. For example, the invention relates to a molded ophthalmic fundus observation or condensing lens which provides for examination of the interior of an eye. The invention relates to molded ophthalmic lenses which can be injection molded and/or, compression molded to provide a single use lens. The ophthalmic lens has an integral ring and aspheric shape differing from known lenses of the same type to reduce cost and improve the optical quality of the lens. As another example, the invention relates contact lenses used by the clinician to view or treat the eye having a main body portion, a grip portion and an eye contacting portion. The invention relates to molded ophthalmic contact lenses which can be injection molded and/or, compression molded to provide a single use lens. The ophthalmic lens has an integral ring and shape differing from known contact lenses of the same type to reduce cost and improve the optical quality of the lens.

In FIG. 1 a molded ophthalmic fundus observation or condensing lens 1 is positioned in close proximity to the patient's eye 2. The lens 1 is formed of an optically transparent material and has a first surface or proximal surface 3 that is positioned facing the patient's eye 2, adjacent to the cornea 5 and a second lens surface or opposing surface 4 that faces the observing ophthalmologist 13.

A light source, not shown, illuminates the fundus of the eye so as to produce light rays, such as the peripheral bundles of light rays 8, 10, emanating from the fundus 6 of the eye 2. The rays diverge from the fundus and pass through the pupil of the eye (dilated or undilated) 12, which is the limiting aperture of the eye. The rays exit the eye at the cornea 5 and are captured by the first surface 3 of the lens 1. The first surface 3 of the lens 1 directs the rays 8, 10 emanating from the eye 2 towards the second lens surface 4 which focuses the rays 8, 10 to respective points 9, 11 so as to form a planar, inverted real image 7 of the fundus 6. The ophthalmologist is able to observe the image 7 of the interior of the eye using, for example, an indirect ophthalmoscope, a refracting scope or even merely a pen light or the like forming the light source illuminating the eye.

The present ophthalmic lens is a molded lens. It can be injection molded and/or, compression molded. The ophthalmic lens of the present invention can be mass produced in large volumes with a high optical quality. This allows for single use lenses which can prevent contamination and disease transmission. Further, because of the single piece nature of the ophthalmic lens of the present invention and the fact that it is comprised of fewer components, the ability to produce the lens for lower cost is realized.

The ophthalmic lens is made of an optically transparent material. The optically transparent material may be any moldable material. For example, it can be a plastic material or other suitable transparent material. In one embodiment, the material is an optical grade acrylic resin such as polymethylmethacrylate (PMMA), styrene, polycarbonate or others well known in the art. The material (e.g. acrylic resin such as PMMA) can have a specific gravity of 1.1-1.9, or preferably 1.1-1.2, or preferably less than 1.19. The material can also have an index of refraction of 1.4-1.55, or preferably 1.49.

Figure 2:
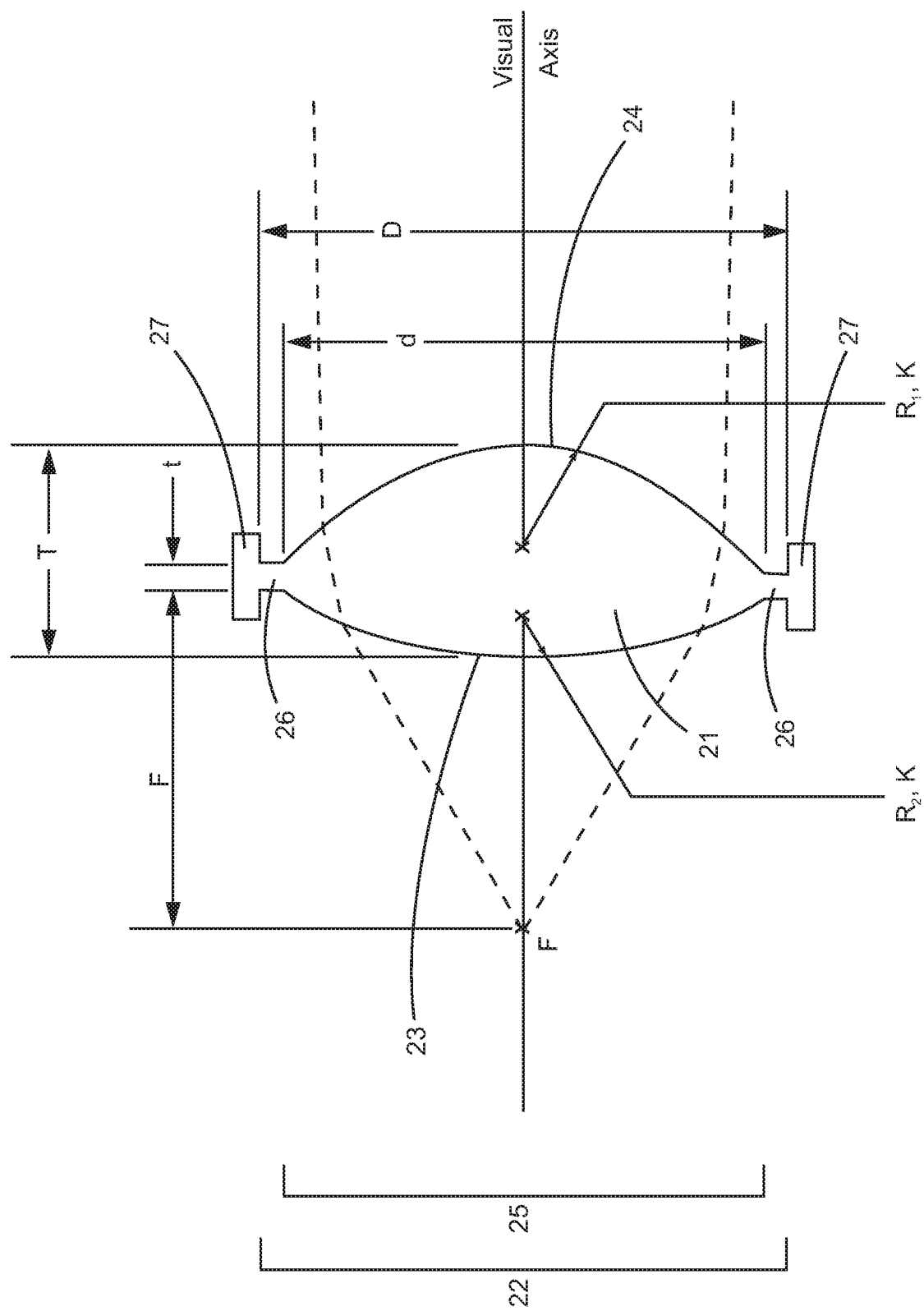
FIG. 2 is a cross-sectional schematic view of a fundus observation lens of one embodiment of the present invention.

FIG. 2 shows an embodiment of a molded ophthalmic lens 21 according to the present application. The ophthalmic lens has a main body portion 22 which includes the optical portion 25. The optical portion is a nonsymmetric lens with two curved, nonspherical surfaces 23 and 24 specifically shaped to capture the image rays from the fundus exiting the pupil of the patient's eye to form a real inverted image of the interior of the eye having minimal distortions. The image rays from the fundus exiting the pupil of the patient's eye enter the lens at surface 23 and exit it at surface 24. The proximal surface of the main body portion 23 is proximal to the eye, but not contacting whilst the opposing surface of the main body portion 24 is away from the eye.

The optical surfaces of the lens 23 and 24 are defined by the following formula:

$$z = Cr^2/(1+\sqrt{(1-(1+K)C^2 r^2)})$$

C=the curvature of the surface at the vertex of the optic
K=the conic constant, a term which flattens the curve with increase in diameter
r=is the variable relating to the optic's diameter and is increased in value from 0 (the vertex of the optical surface), to r max, (r max=½ the diameter of the optic).
z=the geometric depth of a point on the optical surface with respect to r.

For the proximal surface 23 of the main body lens 22, having a magnification of the fundus image of the human eye of 0.67 the following values are preferred:

$$1/C = 14.0 +/- 1.0$$

$$K = -2.0 +/- 0.1$$

For the opposing surface 24 of the main body lens 22, the following values are preferred.

$$1/C = 8.0 +/- 1.0$$

$$K = -2.0 +/- 0.1$$

For an ophthalmic lens 21 having a 0.77 times magnification, the following values for the proximal surface 23 of the main body lens 22 are preferred $1/C = 15.5 +/- 1.0$ $K = -2.0 +/- 0.1$ and the following values for the opposing surface 24 of the main body lens 22 are preferred.

$1/C = 9.6 +/- 1.0$ $K = -1.5 +/- 0.5$

For an ophthalmic lens 21 having a 1.0 times magnification, the following values for the proximal surface 23 of the main body lens 22 are preferred $1/C = 25.0 +/- 1.0$ $K = -1.5 +/- 0.5$ and the following values for the opposing surface 24 of the main body lens are preferred.

$1/C = -11.5.0 +/- 1.0$ $K = -1.5 +/- 0.5$

In accordance with another embodiment of the present invention, the ophthalmic lens 21 includes two aspheric surfaces 23 and 24 each having a vertex radi, $R_1$ for the opposing surface and $R_2$ for the proximal surface. The ratio of the vertex radi of the two surfaces of curvature comparing the proximal surface 23 to the opposing surface 24 ranges between 1.5 and 2.0 times, i.e. the proximal surface is always flatter than the opposing surface. In one embodiment, the proximal lens surface 23 having a vertex radius radius of 14 whilst the opposing surface 24 of the main body lens has a vertex radius of 8.0 for a lens having a magnification of 0.67.

Since the surfaces of the ophthalmic lens are comprised of aspheric curves and given that the curves of the surfaces have a vertex radius where the radius of curvature most proximal to the eye is less steep than the radius of curvature of the surface opposing the eye, the lens works better than previously known lenses for viewing the fundus of patients whose eyes are difficult to dilate, e.g. elderly patients and children. Thus, clinician can also more easily view the interior of the eye for diagnosis and/or treatment.

In order to improve the ophthalmic lens 21 for molding, in one embodiment, the main body portion also has a ring portion 26. As shown in FIG. 2, the ring portion 26 is circumferentially oriented around the main body portion 22 with respect to the visual axis of the ophthalmic lens.

The height of the ring (t) related to the thickness of the lens (T) gives a thickness ratio t/T. The main body portion 22 can have a thickness ratio t/T of 0.1 to 0.2. The diameter of the optical portion (d) related to the diameter of the optical portion 25 and the ring portion (D) gives a diameter ratio d/D. The main body portion 22 can have a diameter ratio of 0.75 to 0.9. The thickness (T) can be from 10 to 20 mm. In one embodiment it is at least 10 mm.

Another important ratio is F/T or focal length over thickness. It can range from 0.6 to 1.0, preferably approximately 0.8.

The shape of the ring portion 26 integral with the optical portion and extending from the main body allows any debris, bubbles and the like that tend to adhere to the surface of the mold during the molding process to collect away from the optical centerline of the lens so as to improve the optical quality of the molded ophthalmic lens. Moreover, the shape of the ring feature also minimizes shrinkage during the molding process.

The ophthalmic lens can also have a grip portion 27 integral with the main body portion 22. In a preferred embodiment, the grip portion 27 is textured so that a clinician can easily maintain his grip on the lens 21 during diagnosis or treatment. The grip portion 27 of the ophthalmic lens 21 may have a generally cylindrical sidewall.

In one embodiment the ring portion 26 can also act as a grip portion for the clinician to easily maintain his grip on the lens 21 during diagnosis or treatment. This can be done, for example, by texturizing the ring portion 27.

The ophthalmic lenses of the present invention are shaped to optimize the molding process of the lenses and improve the optical quality of the lenses. In particular, the ophthalmic lens has an integral ring and aspheric shape differing from known lenses of the same type to reduce cost and improve the optical quality of the lens. Moreover, because the ophthalmic lenses of the present invention are molded as opposed to machined, the ophthalmic lenses of the present invention can be mass produced in volume at low cost. As such, the ophthalmic lenses of the present invention are particularly suitable for single use or disposable applications of the lenses. Because the ophthalmic lenses of the present invention are single use or disposable ophthalmic lenses that may be used once and disposed of, disease transmission via the lenses is substantially minimized.

Figure 3:
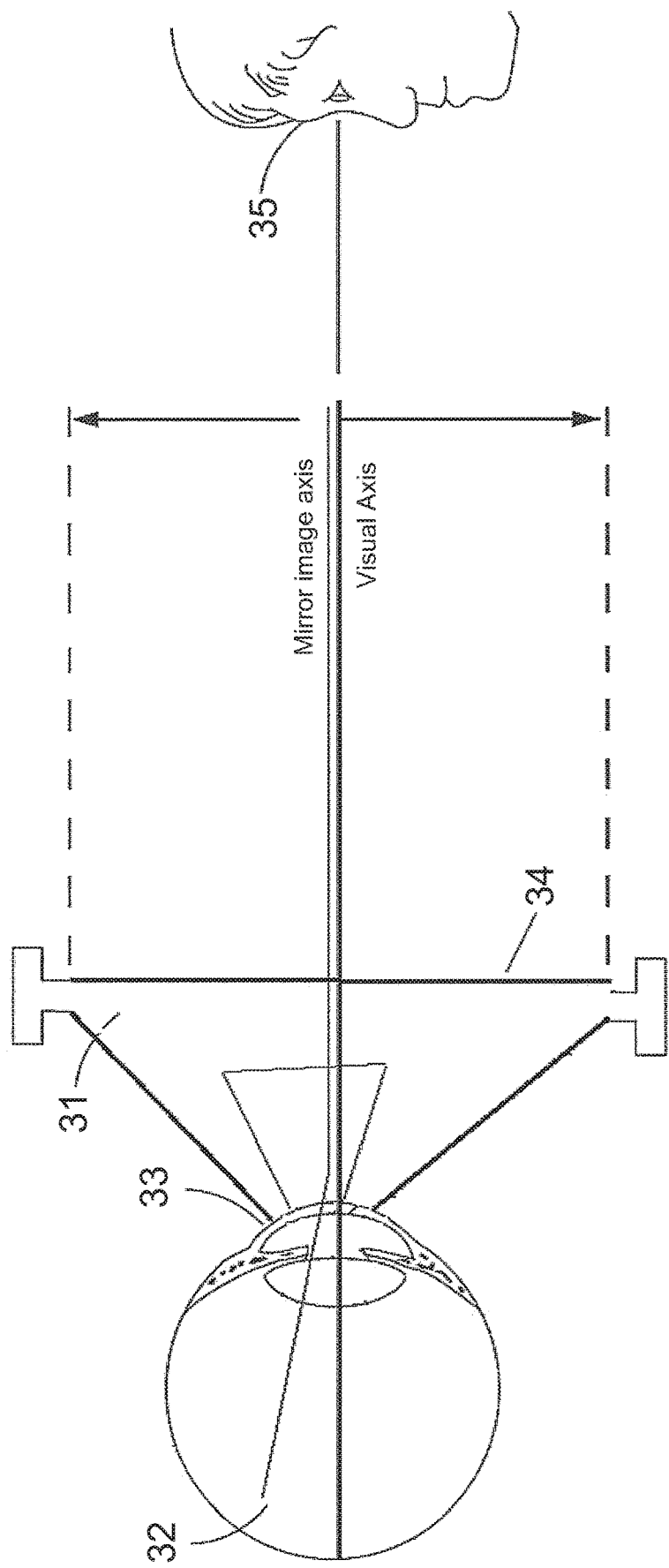
FIG. 3 is a cross-sectional schematic view of a contact lens of one embodiment of the present invention where the lens is in contact with the eye of a patient.

In FIG. 3 a molded ophthalmic contact lens 31 is positioned in contact with the patient's eye 32. The lens 31 is formed of an optically transparent material and has a contact surface that touches the cornea of the patient 33 and a second lens surface or opposing surface 4 that faces the observing ophthalmologist 35.

The present ophthalmic contact lens is a molded lens. It can be injection molded and/or, compression molded. The ophthalmic lens of the present invention can be mass produced in large volumes with a high optical quality. This allows for single use lenses which can prevent contamination and disease transmission. Further, because of the single piece nature of the ophthalmic lens of the present invention and the fact that it is comprised of fewer components, the ability to produce the lens for lower cost is realized.

The ophthalmic contact lens is made of an optically transparent material. The optically transparent material may be any moldable material. For example, it can be a plastic material or other suitable transparent material. In one embodiment, the material is an optical grade acrylic resin such as polymethylmethacrylate (PMMA), styrene, polycarbonate or others well known in the art. The material (e.g. acrylic resin such as PMMA) can have a specific gravity of 1.1-1.9, or preferably 1.1-1.3, or preferably less than 1.3. The material can also have an index of refraction of 1.4-1.55, or preferably 1.49.

FIG. 4 shows an embodiment of a molded ophthalmic contact lens 41 according to the present application. The ophthalmic lens has a ring portion 42. The ring portion can also be attached to or act as a grip portion 43 to be gripped directly or indirectly by a clinician to hold the ophthalmic lens in contact with a patient's eye when the ophthalmic lens is in use. The ophthalmic lens also has an eye contacting portion 44. Between the eye contacting portion 44 and the ring portion 42 is a main body portion 45. The eye contacting portion 44 of the ophthalmic lens is shaped to match a cornea of an eye. In a preferred embodiment, the eye contacting portion 44 of the lens has a diameter of approximately 12.5 mm and a radius curvature of 7.75 mm. The ring portion 42 and/or grip portion 43 of the ophthalmic lens may have a generally cylindrical sidewall. In a preferred embodiment, the grip portion 43 is textured so that a clinician can easily maintain his grip on the lens during diagnosis or treatment. It is noted that, if desired, a larger grip surface may be added over the grip portion 43. The surface of the lens opposite of the eye contacting portion may be planar or curved for magnification.

The main body 45 of the ophthalmic contact lens can also be molded with at least one flat mirror surface 46. For an ophthalmic lens having a single mirror surface, the width of the mirror surface may be at least 6 mm or greater. The thickness, T, of the ophthalmic lens is at least about 21 mm. In a preferred embodiment the mirror surface has an aluminum coating.

FIG. 4 illustrates an ophthalmic contact lens 41 having at least one mirrored surface 46 formed in the—main body portion 45 of the lens 41. The length T of the ophthalmic lens 41 is at least about 16 mm. In a preferred embodiment, the mirrored surface 46 has an aluminum coating.

In order to improve the ophthalmic contact lenses of the present invention, the ring/grip portion 42/43 is circumferentially oriented around the main body portion 45 with respect to the visual axis of the ophthalmic lens.

The height of the ring portion (t) related to the thickness of the lens (T) gives a height of ring to thickness of lens ratio t/T. The ophthalmic lens can have a height of ring to thickness of lens ratio t/T of about 0.1 to about 0.2. The diameter of the optical portion (d) related to the diameter of the optical portion and the ring portion (D) gives a diameter ratio d/D. The ophthalmic lens can have a diameter ratio of about 0.75 to about 0.9. The thickness of the lens (T) can be from about 10 to about 20 mm. In one embodiment it is at least about 10 mm. The height of the ring (t) can be from about 1 to about 7 mm.

The height of the grip portion (W) related to the thickness of the lens (T) gives a height of the grip to thickness of the lens ratio W/T. The ophthalmic lens can have a height of the grip to thickness of the lens ratio W/T of about 0.15 to about 0.3. The height of the grip portion (W) can be from 3 to 10 mm.

The height of the grip portion (W) related to the height of the ring portion (t) gives a height of the grip to height of the ring ratio W/t. The ophthalmic lens can have a height of the grip to height of the ring ratio W/t of about 0.1 to about 1.0.

The shape of the ring portion and/or grip portion extending from the main body allows any debris, bubbles and the like that tend to adhere to the surface of the mold during the molding process to collect away from the optical centerline of the lens so as to improve the optical quality of the molded ophthalmic lens. Moreover, the shape of the ring feature also minimizes shrinkage during the molding process.

The ophthalmic contact lens can also have a grip portion 43 integral with the main body portion 45. In a preferred embodiment, the grip portion 43 is textured so that a clinician can easily maintain his grip on the lens during diagnosis or treatment. The grip portion 43 of the ophthalmic lens may have a generally cylindrical sidewall.

In one embodiment the ring portion 42 can also act as a grip portion 43 for the clinician to easily maintain his grip on the lens during diagnosis or treatment. This can be done, for example, by texturizing the ring portion 42.

The ophthalmic contact lenses of the present invention are shaped to optimize the molding process of the lenses and improve the optical quality of the lenses. In particular, the ophthalmic contact lens has an integral ring differing from known lenses of the same type to reduce cost and improve the optical quality of the lens. Moreover, because the ophthalmic contact lenses of the present invention are molded as opposed to machined, the ophthalmic lenses of the present invention can be mass produced in volume at low cost. As such, the ophthalmic lenses of the present invention are particularly suitable for single use or disposable applications of the lenses. Because the ophthalmic lenses of the present invention are single use or disposable ophthalmic lenses that may be used once and disposed of, disease transmission via the lenses is substantially minimized.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A molded, single-piece ophthalmic lens for examination or treatment of the interior of an eye comprising:
   a ring portion,
   an eye contacting portion and
   a main body portion disposed between the ring portion and the eye contacting portion with the ring portion extending from and circumferentially around the main body portion; and
   wherein the lens has a height of the ring portion (t) to thickness of the lens (T) ratio (t/T) of about 0.1 to about 0.2.

2. An ophthalmic lens as recited in claim 1 wherein said lens is formed of a material having a specific gravity of about 1.1 to about 1.9 and an index of refraction of about 1.4 to about 1.55.

3. An ophthalmic lens as recited in claim 2 wherein said lens is formed of polymethylmethacrylate.

4. An ophthalmic lens as recited in claim 1 wherein said lens comprises an optical portion and has a ratio of the diameter of the optical portion related to the diameter of the optical portion and the ring portion (d/D) of about 0.75 to about 0.9.

5. An ophthalmic lens as recited in claim 1 wherein the lens is formed of a material having a specific gravity of about 1.1 to about 1.3.

6. An ophthalmic lens as recited in claim 1 wherein an axis of rotation of the ring portion is perpendicular with a centerline of the lens.

7. An ophthalmic lens as recited in claim 1 wherein the lens is formed of a material having an index of refraction between about 1.4 and about 1.55.

8. An ophthalmic lens as recited in claim 1 having a thickness of the lens that is at least about 10 mm.

9. An ophthalmic lens as recited in claim 1 further comprising a grip portion integrally connected to said ring portion.

10. An ophthalmic lens as recited in claim 9 having a height of the grip portion to thickness of the lens ratio of about 0.15 to about 0.3.

11. An ophthalmic lens as recited in claim 9 wherein the grip portion is textured.

12. An ophthalmic lens as recited in claim 9 wherein a height of the grip portion is about 3 mm to about 10 mm.

13. An ophthalmic lens as recited in claim 9 wherein a height of the grip to height of the ring portion ratio is about 0.1 to about 1.0.

14. An ophthalmic lens as recited in claim 1 wherein a height of the ring portion is about 1 mm to about 7 mm.

15. An ophthalmic lens as recited in claim 1 wherein a thickness of the lens ranges from about 10 to about 20 mm.

16. An ophthalmic lens as recited in claim 1 wherein said lens is disposable.

17. An ophthalmic lens as recited in claim 1 further including an aluminum coating on a mirror surface.

18. An ophthalmic lens as recited in claim 1 having a single mirror with a width that is at least about 13.7 mm.

* * * * *